United States Patent [19]

Riemann

[11] Patent Number: 4,964,971

[45] Date of Patent: Oct. 23, 1990

[54] LIQUID ANALYZER

[76] Inventor: Werner H. Riemann, Heinrich-Heine-Strasse 26, D-3550 Marburg (Lahn), Fed. Rep. of Germany

[21] Appl. No.: 180,459

[22] Filed: Apr. 12, 1988

[30] Foreign Application Priority Data

Apr. 14, 1987 [DE] Fed. Rep. of Germany ... 8705520[U]

[51] Int. Cl.$^5$ .......................................... G01N 27/416
[52] U.S. Cl. ..................................... 204/403; 204/409
[58] Field of Search ............... 204/401, 403, 409, 411, 204/412, 416

[56] References Cited

U.S. PATENT DOCUMENTS 4,758,325  7/1988  Kanno et al. ........................ 204/411

*Primary Examiner*—G. L. Kaplan
*Attorney, Agent, or Firm*—Fred Philpitt

[57] ABSTRACT

The invention relates to an analyzer for liquids with at least one module (10) including a measuring line (14) having a reference electrode (16) and at least one measuring electrode (18). Measuring pads (48) borne by a carrier (80) can be pressed onto the measuring line; when out of contact therewith, they can be moved to and fro. The carrier may be elongated and adapted for sliding along a guiding rod (76). A spring-biased bar parallel thereto is pivotable and guides the carrier (80) as the latter is moved, e.g. when engaged by a tappet (68) of a motor-driven crank disk (66). A module chamber (30) is flow-connected to the measuring line (14) via a capillary aperture (28) in a flexible supply tube (26). Expediently, the capillary aperture (28) limits the leakage of an electrolyte in the chamber (30) to a maximum rate of 0.1 μl per 24 hours at ambient pressure and ambient temperature.

20 Claims, 6 Drawing Sheets

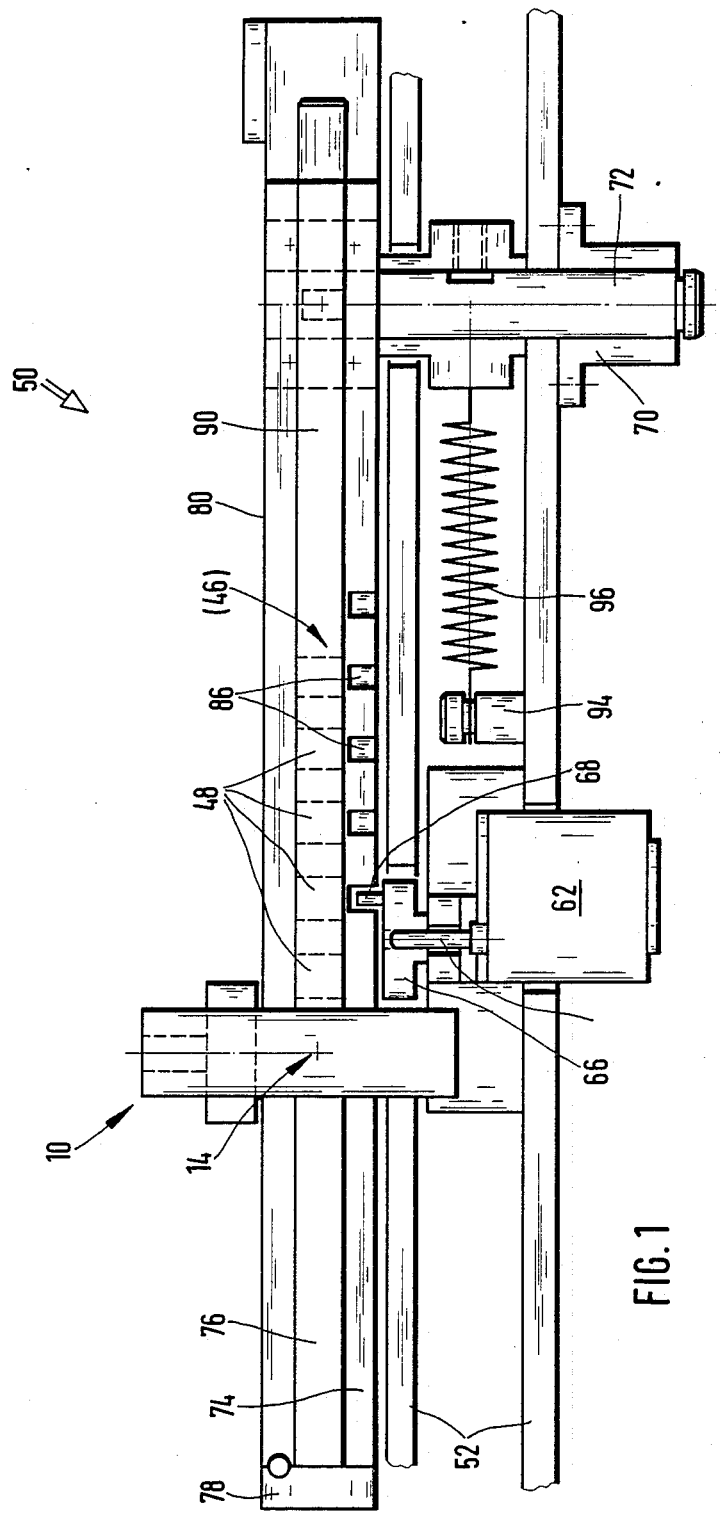

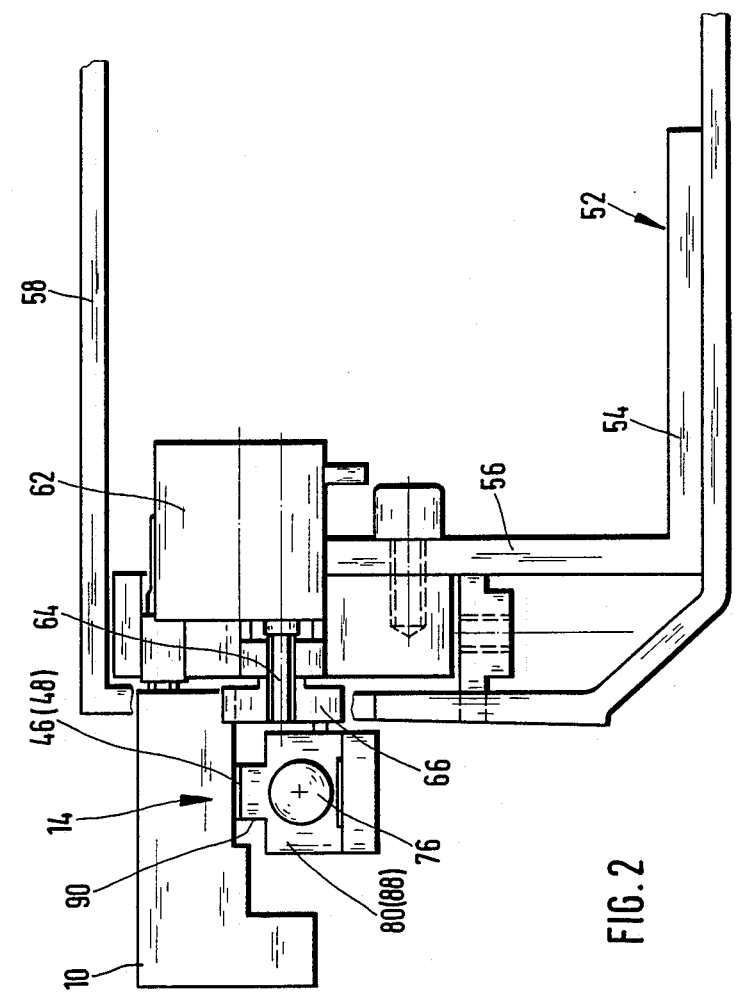

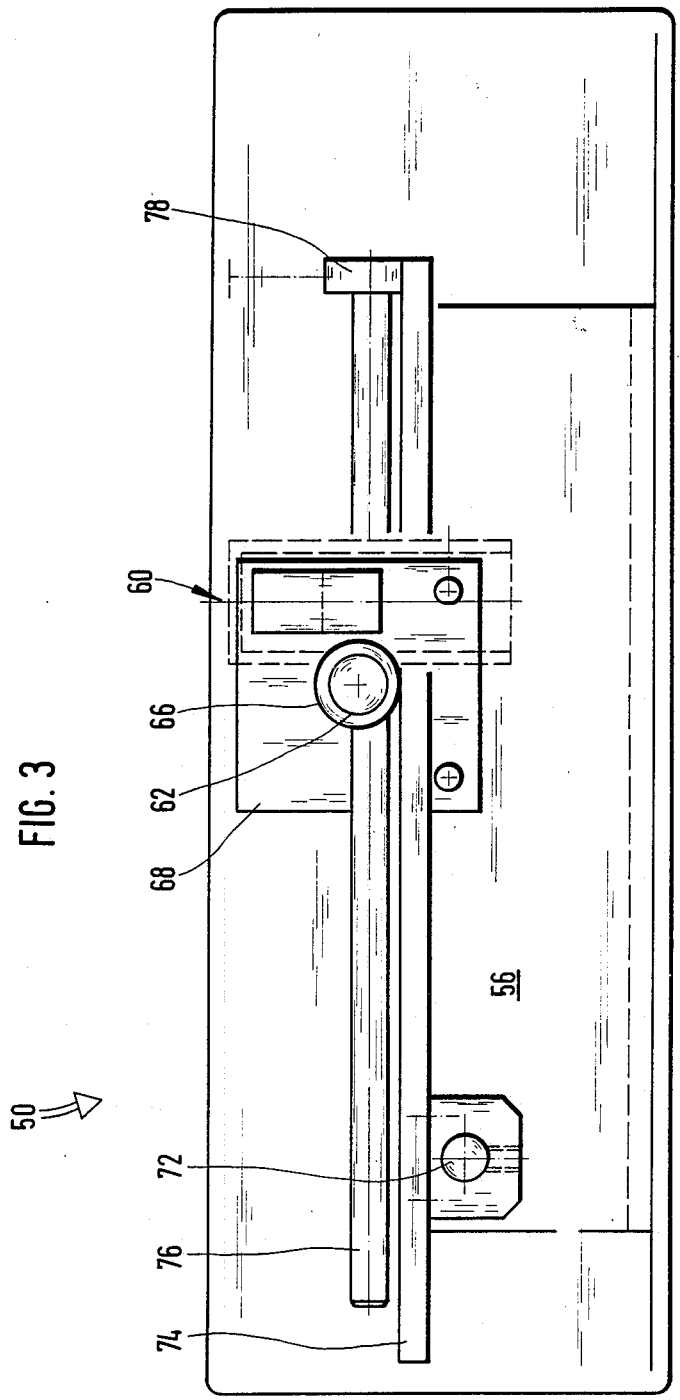

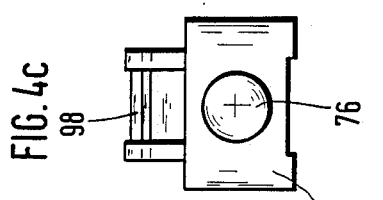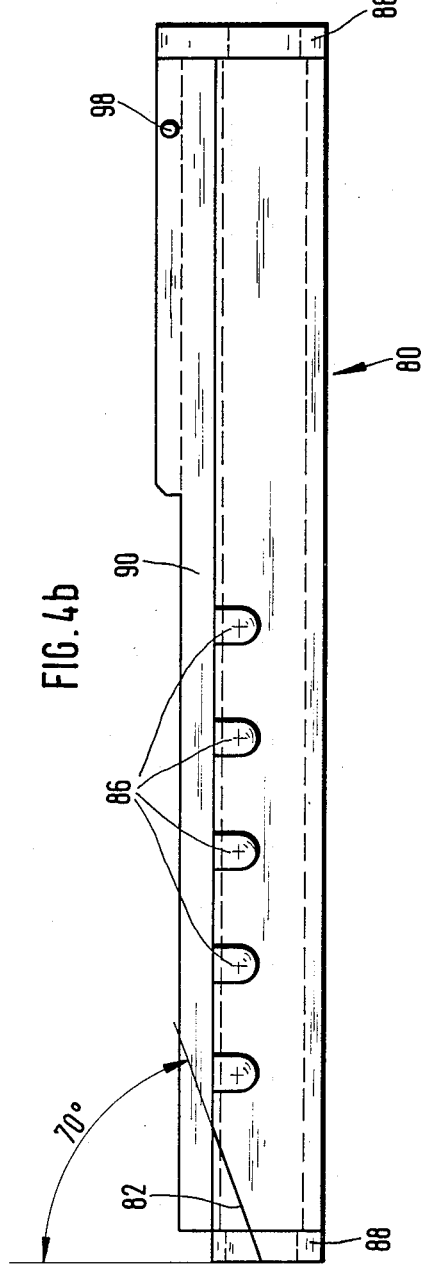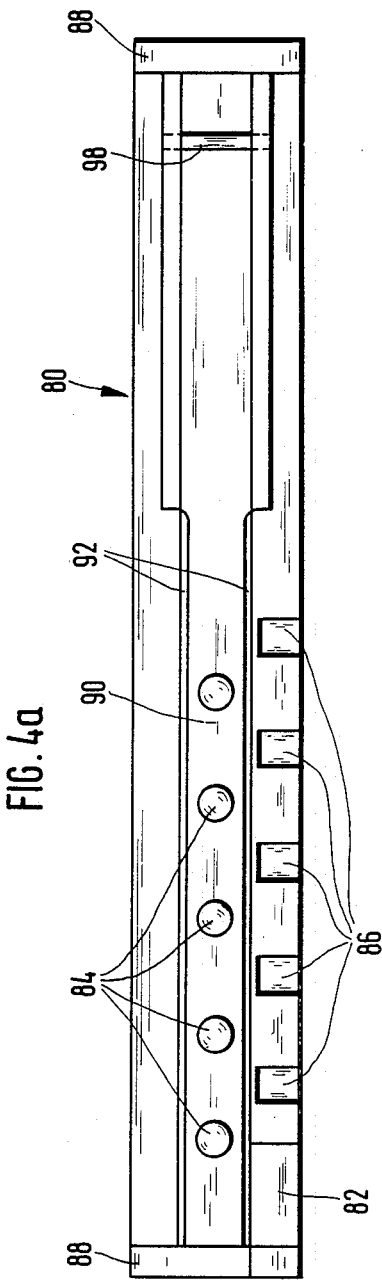

LIQUID ANALYZER

The present invention relates to a liquid analyzer.

Analyzers have been used for some time in large clinics having automated analytic systems including ion-selective electrodes. The conventional devices require considerable expenditure, as is evident from DE-OS 14 98 576, from GB-PS 2 000 297 and from DE-U-77 18 736, to quote exemplary apparatus involving a measuring line through which the liquid to be analyzed is passed, e.g. by means of a peristaltic pump. Two or more reference and measuring electrodes arranged in series extend into a bore forming the measuring line and are electrochemical half cells which selectively respond to certain types of ions.

At the entrance of a conventional analyzer, the samples—for example, liquids containing organic and inorganic matter—are picked up by means of an intake tube. Vessels containing the samples to be measured must be successively moved below the intake tube which is then submerged in the respective sample to fetch part of it. The length of the tube connection between the lower opening of the intake tube and the measuring means in the analyzer, viz. a mesuring cell or a sensor, is a nasty spurce of contamination. Even where the connection materials are hardly wettable, a thin film of liquid will adhere to the inner and outer walls. The inevitable entrainment causes faults in the order of ±5 percent, the error increasing with the connection length as well as its diameter; moreover, it will grow the more the liquids adheres to the connection material and the larger the differences of concentration of successive samples are. Particularly large faults occur with viscous and albuminous liquids such as whole blood or serum. A considerable part of the contamination is due to the intake tube whose lower end is successively dipped into each sample and is, therefore, wetted both inside and outside.

It has been attempted to reduce the carry-out by air bubbles between the samples and by intercalation of scavenging and cleaning baths. Still, the difficulties mentioned could hitherto not be eliminated to a satisfactory extent.

Consequently, there is a desire to solve the problem in a simple and economic manner. It is an important object of the invention to develop a handy-sized mobile device which will, above all, minimize contamination faults. The invention also aims at creating a rather low-priced analyzer suitable for use by smaller firms and offices of medical practitioners, laboratories and clinics.

According to the invention, there are means for the controlled movement of a carrier of measuring pads towards a measuring line and for pressing onto the same, and further means for moving the carrier back and forth when the measuring pads are out of contact with the measuring line which includes a channel, bore or the like as weel as a reference electrode and at least one measuring electrode. Such arrangement affords relatively small expenditure and is suitable for a compact design. The device, therefore, can be used without complex installation at a multitude of locations. The requisite measurements are carried out fast and with a high degree of accuracy.

The module which comprises the measuring line may advantageously be above the carrier in an inverted position thereto so that the respective pads will be moved upwards for contact with the line. Thus dripping and spilling of liquid will be avoided, whilst the pads can be kept in a substantially horizontal position so that they will remain moist for long periods of time.

The carrier may be moved by electromechanical and/or electromagnetic means. A crank-like movement can be achieved through a pivotable guide bar on which the carrier is shiftable in steps, e.g. using a motor-driven crank dish whose tappet engages lateral recesses or notches of the carrier. On top of the latter, a strip may be held which includes an array of measuring pads and an end of which may be confined for secure movement with the carrier.

An extremely compact design of the measuring module is obtained by a chamber which is adapted to be sealed, to extend up to the measuring line and to be flow-connected therewith through a capillary aperture. Any piston pipette will do to apply a calibrating liquid or the liquids to be measured; if throw-away tips are used, contamination problems can be reduced to an absolute minimum. There will be no long tubes or complicated tube connections, pumps and valves. As a result, adhesion difficulties at the inner and outer portions of connection components are done away with.

A favorable structure is achieved if the chamber is designed as a bore that extends across the measuring line and that is sealed at either end. While one end is preferably sealed by the reference electrode, the other end may be opened, if need be. It is expediently sealed by a semi-permeable disk through which very small quantities of air may enter into the chamber in order to prevent vaccumizing which might impede the —extremely slow—outflow of an electrolyte. The design warrants that the contact electrolyte cannot exude at any other point. Important features of the invention include the dimensioning, relative to the inner bore diameter, of the capillary aperture on the one hand and of the chamber on the other hand. The clear width of the capillary aperture may be smaller than 1 $\mu$m.

The supply tube may be flexible and be sealingly attached to the chamber walls, terminating in the measuring line, in particular with matching diameters so as to provide minimum flow resistance.

Plug connector means will permit the module to be quickly attached to an instrument for null balancing and following measurements of potential differences. Various pins may serve to provide code connections for selecting specific ion detection. Further features, particulars and advantages of the invention will be apparent from the wording of the claims and from the following description of preferred embodiments shown in the annexed drawings wherein:

FIG. 1 is a top view of part of an opened device according to the invention,

FIG. 2 is a partial end view of the device of FIG. 1,

FIG. 3 is a rear view of the device shown in FIGS. 1 and 2,

FIG. 4a is a top view of a carrier,

FIG. 4b is a side elevation of the carrier shown in FIG. 4a,

FIG. 4c is an end view of the carrier shown in FIGS. 4a and 4b,

Figure 7:
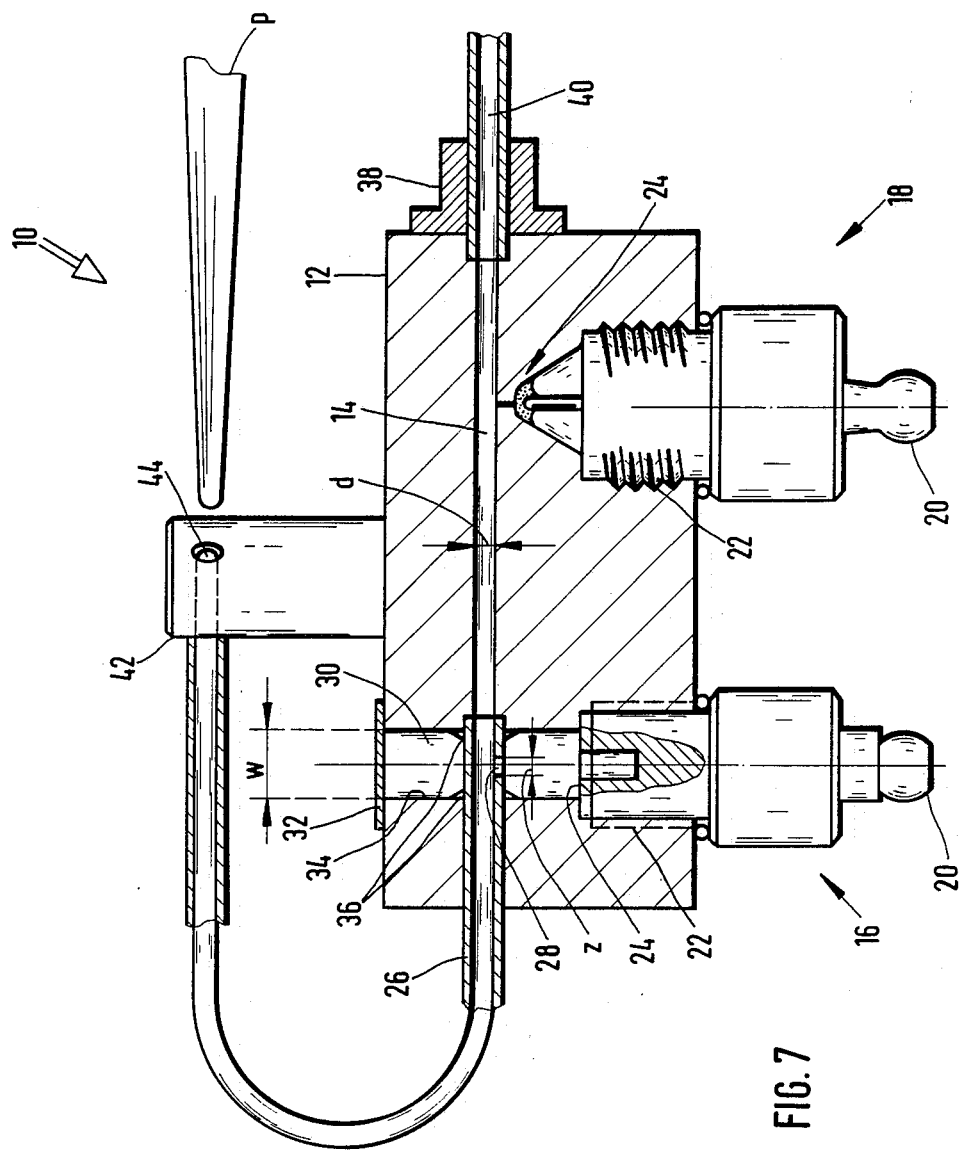
FIG. 7 is a side view, partly sectionalized, of another module embodiment.

As will be evident from FIG. 7, a module 10 to be used in an analyzer device according to the invention has a body 12 with a measuring line 14 by way of a channel or bore whose inner diameter d may, for example, be 0.5 mm. With a probe portion 24 each, a reference electrode 16 and a measuring electrode 18 extend to the measuring line 14 at one side of the body 12. Each of the electrodes 16, 18 includes a connector 20 as well as a threaded section 22. Although only one measuring electrode 18 is shown, there may be a plurality of measuring electrodes in the module 10. Owing to the threaded sections 22, the electodes 16, 18 may be exchanged quickly. O-ring seals may be provided at the body exterior for additional obturation.

A supply tube 26, preferably inner diameter d, leads to the measuring line 14. Opposite to the reference electrode 16, the end of the supply tube 26 which joins the measuring line 14 is provided with a capillary aperture 28 whose clear width z is extremely small, for example smaller than 1 $\mu$m.

In the region of the reference electrode 16, the body 12 is passed by a bore or chamber 30 in a direction transverse to the measuring line 14. The chamber 30 is a tank for the contact electrolyte employed and may have a diameter w=4 mm as well as a length of 9 mm. At one end, the bore 30 is sealed by the plane face of the reference electrode 16. The other end is sealed by a semi-permeable disk 32 that may be of silicon caoutchouc and may be adhesively attached to the adjacent outer wall of the body 12. The latter is preferably of polymethylmethacrylate, whereas the supply tube 26 and an outlet 40 may be tube material of soft polyvinyl chloride with an outer diameter of, say, 1 mm. Where the supply tube 26 crosses the chamber walls 34, it is sealingly affixed thereto by adhesive seams 36. Instead of those, it is also possible to provide suitable sealing components.

The outlet 40 is held in a socket 38 of the body 12. The supply tube 26 is mounted in a projection 42 of the body 12 having a transverse bore with an orifice 44. In order to fill a liquid to be analyzed into the module 10, a pipette P is used for injection into the orifice 44 as indicated.

The device shown in FIGS. 1 to 6 is generally designated by 50. It comprises a frame 52 with an angle member 54 that includes a wall support 56. A top 58 shown in FIG. 2 is removed in FIG. 1 for the sake of clarity.

A motor 60 and a gear 62 are mounted to the wall support 56. The output shaft 64 of the gear 62 carries disk 66 which bears a tappet 68 that is eccentric relative to the axis of rotation of the crank disk 66. This drive system serves to operate a carrier 80 (see, in particular, FIGS. 4a, 4b, 4c in combination with FIGS. 1 and 2). The carrier 80 is, in fact, a carriage slidably arranged on a guide bar 74 which holds a parallel rod 76 attached by means of an end plate 78.

It will be seen from FIGS. 4a to 4c that the carrier 80 features a run-in slope 82 at a front end. It is generally of square shape, having an upper central rib 90 and lateral flutes 92 for ease of applying and removing a measuring strip 46 placed on top of the rib 90 for the analyzing measurements to be performed. The strip 46 will be held down by a confining bar 98 preventing the strip end from rising. the measuring strip 46 comprises an array of pads 48 designed to receive the various liquids to be analyzed. As a substitute or in addition, the central rib 90 may be provided with a series of pits 84 as indicated in FIG. 4a.

On at least one side, the carrier 80 has recesses 86 shaped as notches which can successively be engaged by the tappet 68 as the crank disk 66 rotates. The carrier 80 is further rigidly connected to a shaft 72 arranged transversely thereto and supported in a bearing 70 held by the frame 52. To the latter, there is also secured a stud 94 onto which one end of a spring 96 is hooked whose other end is affixed to the shaft 72 and thus to the carrier 80. It will be noted that the carrier 80 is pivotable around its shaft 72 in the bearing 70 so that its main portion will be lowered relative to the frame 52. The lowering movement as well as a subsequent advance movement will be effected by the crank-tappet system 66/68 engaging the notches 86 of the carrier 80. A return movement can be achieved by reversing the sense of rotation of the crank disk 66.

Since the device 50 includes a module 10 arranged such that the measuring line 14 points downward, it will be appreciated that the measuring strip 46 on top of rib 90 of the carrier 80 will be lowered in respect to the measuring line 14 when out of contact therewith. By an advance or return movement of the carrier 80, one of the pads 48 of the measuring strip 46 will approach the measuring line 14 onto which it is eventually pressed from below. The measurement desired can now be effected.

Preferably, the pads 48 are distributed in such manner that a dry pan will be framed by moist pads in either direction. It is expedient to have a neutralizing pad first, followed by a dry pad, which is succeeded by a moist pad of a first standard, which is followed by another dry pad, the last in the row being another moist pad of a second standard. Once the device 50 has been calibrated in this order, further strips 46 are used for measurements of one specific ion type each. For safe analysis, it is preferred to have null balancing effected on the first and third pads, the second and fourth pads being dry for removal of contaminating liquid remainders, whereupon the fifth pad with an actual sample may be analyzed.

The pressing force with each pad 48 will be engaging the measuring line 14 may be adjusted as required, e.g. by tensioning or changing the spring 96.

The drive system is suitably provided with positioning and signalling means in order to warrant that one and the same initial position of the crank disk 66 and thus of the tappet 68 be taken after each stop and go. Photoelectric light barriers on the periphery of the crank disk 66 are used to advantage for establishing a defined basic position thereof.

Figure 5:
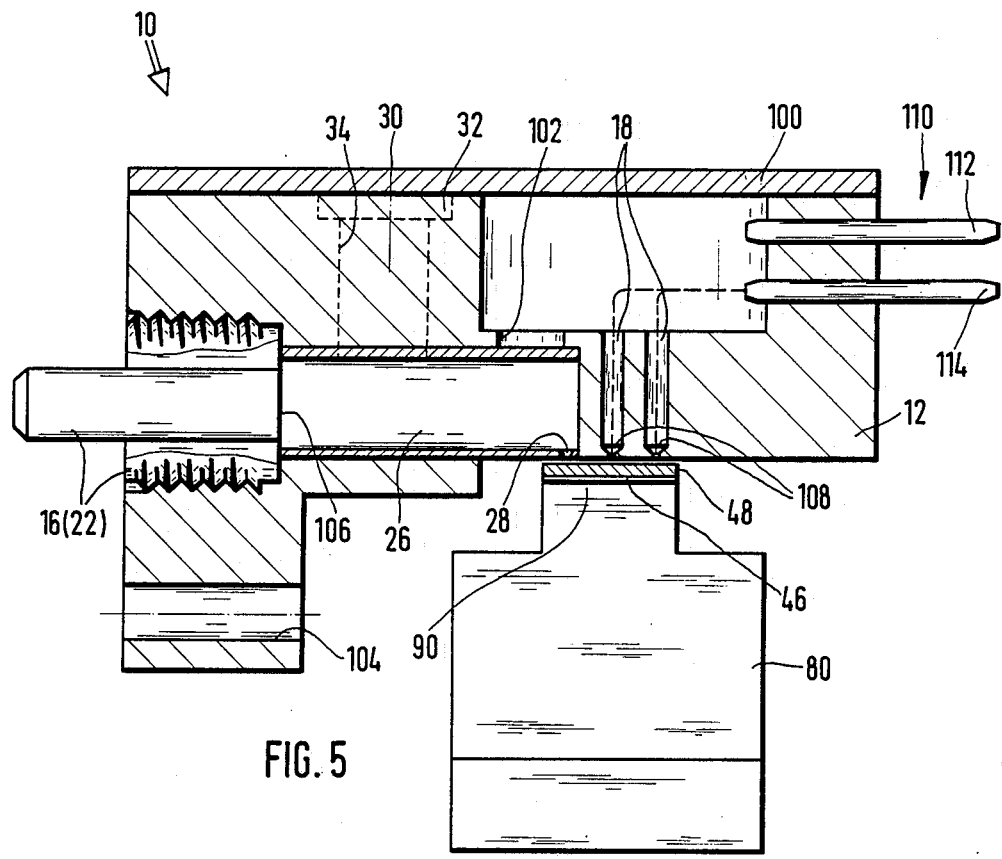
FIG. 5 is a partial section of a module for a device such as shown in FIGS. 1 to 3.
Figure 6:
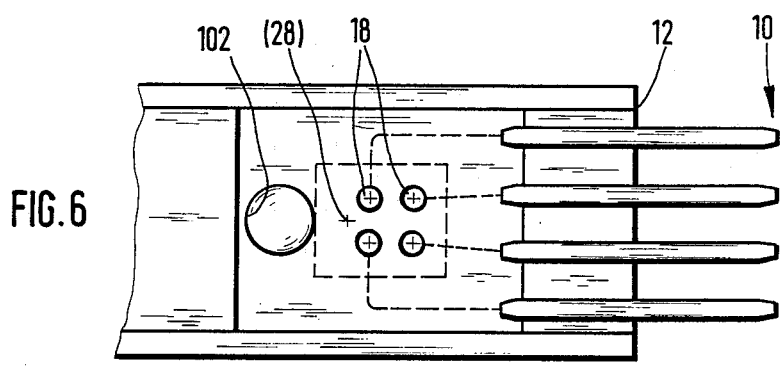
FIGS. 6 is a partial top view of the module of FIG. 5, a top cover being omitted.

Specific features of another module embodiment are shown in FIGS. 5 and 6. The body 12 of the module 10 illustrated there is closed by a cover 100. For pressure balancing, a window 102 is provided adjacent the end of the supply tube 26 that is close to the measuring electrodes 18 of which a set is used here. They are connected to a multiple connector 110 comprising an upper row 112 of pins for coding and selecting the various ion types to be analyzed, and further comprising a lower row 114 carrying the signal voltages of the electrodes selected. For selection, a key block (not shown) can be employed.

A centering bore 104 is advantageous for attaching the module 10, whereby the plug pin of the reference electrode 16 and a guide pin (not shown) fitting the centering bore 104 will be engaged at the same time and will thus safeguard correct mounting of the module 10.

FIG. 5 also shows a pole face 106 of the reference electrode 16, which pole face 106 is a thin sealing member thereto. Preferably, the reference electrode 16 is of the Ag/AgCl system.

As an alternative to the window 102 mentioned above, chamber 30 with seal 32 and walls 34 may be arranged as indicated with dotted lines in FIG. 5, so that a separate window 102 may be dispensed with. However, it may also be retained in case the tank volume available is to be increased.

It will be noted that the measuring electrodes 18 have narrowed lower ends shaped as nozzles 108 (FIG. 5).

Special advantages of the invention reside in the fact that the device 50 and the modules 10 permit mobile use by the patient's bedside; by contrast, the conventional analyzer systems are far too large and too heavy for such migratory application. Another ermit of the invention is to low cost of manufacture as compared to the prior art systems.

Whilst the latter require large sample volumes and can, therefore, be employed with batch type measurements only, the device and module according to the invention are also suitable for continuous analysis. A sample volume of only about 5 to 30 μl each will suffice for an individual analysis.

It will be noted that the device and module according to the invention make possible on-the-spot laboratory findings which will enable a physician to provide direct diagnostics so that he or she is in a position to not only obtain the anamnesis but also to take therapeutical decisions right away.

The apparatus according to the invention are suited for use in clinics and hospitals of moderate means, and also where external energy cannot readily be supplied, e.g. in the developing world. In addition to rapid analyses, application in research and development projects is possible, too. By means of an interface, the equipment can easily be connected to micro-computers of whatever make.

The analysis can be extended to a multitude of organic and inorganic substances, merely by fitting the basic device with sensors as required. New measuring electrodes can be mounted at any time, and even a small assortment of sensors may well replace a large laboratory unit. All the important types of ions can be analyzed without difficulty, including $Na^+$, $K^+$, $Ca^{++}$, $Mg^{++}$, $Li^+$, $NH_4^+$, $Cl^-$, $H^+$ ($p_H$), etc. Due to the very small quantities needed, it will do to take a blood sample by piercing an earlobe or a fingertip.

While preferred embodiments have been illustrated and explained hereinabove, it is to be understood that numerous variations and modifications will be apparent to one skilled in the art without departing from the principles of the invention which, therefore, is not to be construed as being limited to the specific forms described.

I claim:

1. A device for electrochemically analyzing a body fluid which includes in combination
   (a) a frame (52),
   (b) module (10) on said frame (52), said module including a measuring line (14) containing a channel for the body fluid and at least one measuring electrode (18) and at least one reference electrode (16),
   (c) a carrier (80, 46) containing a plurality of measuring pads (48),
   (d) means for the controlled movement of said carrier (80, 46) towards said measuring line (14) and pressing it against said measuring line (14) and
   (e) means for moving the said carrier (80) back and forth relative to the measuring line (24) when the measuring pads are out of contact with the measuring line (14).

2. A device according to claim 1 wherein said module (10) is positioned above the carrier (80) and in an inverted position relative to it.

3. A device according to claim 1 wherein electromechanical and/or electromagnetic means moves the carrier (80).

4. A device according to claim 1 wherein the frame (52) includes a bearing (70) for a guide bar (74) that is pivotable against the force of a spring (96) and that supports a carrier (80) adapted for stepwise shifting so as to singly move the measuring pads borne thereby towards and onto the measuring line (14).

5. A device according to claim 4 wherein the carrier (80) includes caps (88) which are adapted to slidably move along a rod (76) that is parallel to the guide bar (74).

6. A device according to claim 4 wherein the carrier (80) contains lateral recesses (86) for engagement by a tappet (68) of a motor-driven crank disk (66).

7. A device according to claim 6 wherein the crank disk (66) includes positioner means for establishing a defined initial position.

8. A device according to claim 1 wherein the carrier (80) includes an insert strip (46) having an array of measuring pads (46) that are adapted to hold liquid samples.

9. A device according to claim 8 wherein the carrier (80) includes confining means (98) for the strip (46).

10. A device according to claim 1 wherein each of the module electrodes (16, 18) has a connector (20) as well as a threaded section (22) and a probe portion (24) extending towards and onto the measuring line (14) and a chamber (30) in the module (10) is provided which is adapted to be sealed, to extend up to the measuring line (14) and to be flow-connected therewith via a capillary aperture (28).

11. A device according to claim 10 wherein the chamber (30) is arranged in the region of one electrode (16) in a direction transverse to the measuring line (14) and a supply tube (26) that includes the capillary aperture (28) extends through the chamber in a sealed manner.

12. A device according to claim 11 wherein the supply tube (26) is made of polyvinyl chloride and is adhesively attached to the chamber walls (34), the transitions between the supply tube and the tube and the chamber walls comprising adhesive seams (36).

13. A device according to claim 11 wherein the supply tube (26) passing through the chamber (30) is adapted to directly terminate the measuring line (14).

14. A device according to claim 10 wherein the chamber (30) is designed as a bore that is sealed at either end and extends across the measuring line (14).

15. A device according to claim 14 wherein the clear width (z) of the capillary aperture (28) is no larger than one tenth of the bore diameter (d).

16. A device according to the claim 15 wherein the clear width (w) of the chamber (30) is about ten times larger than the inner bore diameter (d) width is no larger than 1.0 mm.

17. A device according to the claim 10 wherein the chamber (30) is sealed by the reference electrode (16) on the one hand and by a semi-permeable disk (32) on the other hand.

18. A device according to the claim 10 wherein the capillary aperture (28) is dimensioned so that the rate of outflow of an electrolyte in the chamber (30) is smaller than 0.1 µl per 24 hours at ambient pressure and ambient temperature.

19. A device according to claim 1 wherein an outlet (40) joining the measuring line (14) is designed to include a pivotable bend.

20. A device according to claim 1 wherein there are plug connector means made up of the electrode connectors (20) associated with each electrode (16, 18).

* * * * *